United States Patent [19]

Burns et al.

[11] Patent Number: 4,638,051

[45] Date of Patent: Jan. 20, 1987

[54] BRAIN IMAGING RADIOPHARMACEUTICALS

[75] Inventors: Hugh D. Burns, BelAir; Susan E. Zemyan; Leon A. Epps, both of Baltimore; Alfred V. Kramer; Robert F. Dannals, both of Baltimore, all of Md.

[73] Assignee: The Johns Hopkins University, Baltimore, Md.

[21] Appl. No.: 723,011

[22] Filed: Apr. 17, 1985

Related U.S. Application Data

[63] Continuation-in-part of Ser. No. 605,368, Apr. 30, 1984, abandoned.

[51] Int. Cl.$^4$ ............................................. C07F 11/00
[52] U.S. Cl. ...................................... 534/14; 424/1.1; 564/500
[58] Field of Search ...................... 534/14; 260/429 R; 564/500

[56] References Cited

U.S. PATENT DOCUMENTS

4,434,151  2/1984  Byrne et al. .
4,444,690  4/1984  Fritzberg .................. 260/429 J

FOREIGN PATENT DOCUMENTS

57-212193  12/1982  Japan .............................. 260/429 R

OTHER PUBLICATIONS

Dannals, et al., "The Use of $^{99}$Tc and $^{99m}$Tc in the Development and Characterization of New Radiotracers for Diagnostic Nuclear Medicine, *Applications of Nuclear and Radiochemistry*, 1982, pp. 127–138.
Chemical Abstracts 98 49645b (1983).
Jones et al., The Journal of Nuclear Medicine, vol. 23, pp. 801–809.
Fritzberg et al., The Journal of Nuclear Medicine, vol. 22, pp. 51, 52, 258–263, vol. 23, pp. 17, 592–598.
Costello et al., Journal of Nuclear Medicine, vol. 24, p. 353.
Davison et al., Journal of Nuclear Medicine, vol. 20, p. 641.
Jones et al., Abstracts of the Fourth International Symposium on Radiopharmaceutical Chemistry, Aug. 1982, p. 333.
Klingensmith et al., The Journal of Nuclear Medicine, vol. 22, p. 38.
Klingensmith et al., The Journal of Nuclear Medicine, vol. 24, p. 80.
Costello et al., The Journal of Nuclear Medicine, vol. 24, pp. 353–355.
Davison et al., Inorganic Chemistry, vol. 20, pp. 1629–1633.
Orvig et al., The Journal of Nuclear Medicine, vol. 20, p. 653.
Fowler et al., The Journal of Nuclear Medicine, vol. 22, pp. P57–P58.
De Pamphilis et al., Proceedings 3d International Symposium on Radiopharmaceutical Chemistry, Jun. 16–20, 1980, pp. 146–147.
Subramian et al., The Journal of Nuclear Medicine, vol. 24, p. 80.
Klingensmith et al., The Journal of Nuclear Medicine, vol. 23, pp. 377, 379.

*Primary Examiner*—Helen M. S. Sneed
*Attorney, Agent, or Firm*—Cushman, Darby & Cushman

[57] ABSTRACT

The present invention relates to coordination compounds of technetium-99m and chelating agents (ligands) for synthesizing them. The technetium compounds are useful as diagnostic brain imaging radiopharmaceuticals.

9 Claims, No Drawings

BRAIN IMAGING RADIOPHARMACEUTICALS

This application is a continuation-in-part of Ser. No. 605,368 filed Apr. 30, 1984, now abandoned.

BACKGROUND OF THE INVENTION

Brain perfusion imaging with single-photon emission computerized tomography is a method of assessing regional perfusion, i.e., the quantities of blood distributed to various parts of the brain. The data generated provides information which is useful for determining metabolic activity in various parts of the brain, for example in assessing the effects of stroke. Its successful application requires imaging agents which can be administered intravenously, and which pass the blood-brain barrier to enter brain tissue.

Useful brain imaging agents require a radioactive element and structure which causes the agent to be transported in the blood, to pass from the blood across the blood-brain barrier and to be retained in brain tissue sufficiently long to measure its concentrations in various parts of the brain. Desirably, 100% of the imaging agent which flows to a particular part of the brain is absorbed into brain tissue, and that agent remains in the brain tissue for about four to six hours so that its concentration (and therefore the amount of blood which flowed to that part of the brain) can be determined. Initial consideration was given to compounds containing radioactive isotopes of iodine and selenium, i.e., I-123, I-125, I-131 and Se-75. Selenium-75 gives poor imaging characteristics; its radiation levels are too high and its half-life is too long. Therefore it can expose patients to the risk of excessive doses of radiation. Iodine-131 suffers from the same difficulties. Iodine-125 has too long a half-life and too low gamma intensity. Iodine-123 is useful, and has been the subject of preliminary clinical studies in the form of N-isopropyl-p-[I-123]iodoamphetamine which provided remarkable results. However I-123 is very expensive and not readily available. Therefore, attention has turned to compounds based on technetium-99m which has the same advantages as Iodine-123, and which is relatively inexpensive and readily available; it is currently the radionuclide which is most widely used for a variety of diagnostic nuclear imaging procedures.

Investigations have been conducted using technetium-99m-labeled 1,2-dithia-5,8-diazacyclodecane, and the results were reported by Kung et al in The Journal of Nuclear Medicine, Vol. 25 pages 326–332. These compounds were found to effectively cross the blood-brain barrier. However, they are retained in brain tissue for only relatively short times.

SUMMARY OF THE INVENTION

The present invention is concerned with ligands and coordination compounds which they form with technetium-99m (Tc-99m). The compounds of the present invention are polyaminodithiols which form stable, neutral complexes with Tc-99m; those complexes are capable of crossing the blood-brain barrier and being retained for a sufficient length of time to be useful as brain imaging agents. These compounds have the following general structure:

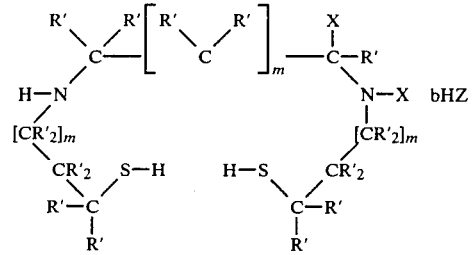

wherein each R' is independently a hydrogen atom, an alkyl group, or substituent X which has the following formula:

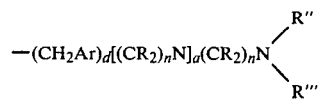

where m is 0 or 1, Z is the anion of a strong mineral acid such as chloride, b is an integer of 2 or greater, preferably 2 or 3 and where R" and R'" are independently hydrogen atoms or alkyl groups, any additional X is R', Ar is an aromatic group such as phenylene, and a, d and n are integers. Preferably a and d are 0 or 1 and n is 2 or 3.

PREFERRED EMBODIMENTS

The compounds of the present invention may be synthesized in neutral base form, but the Tc-99m complexes are synthesized from acid addition salts with sufficient equivalents of an acid, preferably a strong mineral acid such as hydrochloric acid, to correspond to the number of amino groups.

Preferred alkyl groups are lower alkyl groups such as methyl, ethyl, isopropyl and n-propyl, although higher alkyl groups may be used. The groups R" and R'" may be joined to form a heterocyclic ring including the nitrogen of the alkyl-amino side chain X, such as a morpholino group. In general higher alkyl groups will increase the lipophilic character of the compounds which will tend to increase the retention in the brain. On the other hand, an increase of lipophilic character will increase the binding of the compounds to plasma protein and reduce their ease of transport across the blood-brain barrier. The overall lipophilicity of the compounds can be assessed by determining the octanol/saline coefficient, which should be in the range of about 0.5–100. This value is determined by mixing the compounds with octanol and saline solution (0.9% in water) and measuring the proportion of the compound which dissolves in the respective layers. More accurate information can be derived in biodistribution studies in mice.

The following are examples of groups X, and R' in representative compounds according to the invention:

| X | R' |
|---|---|
| 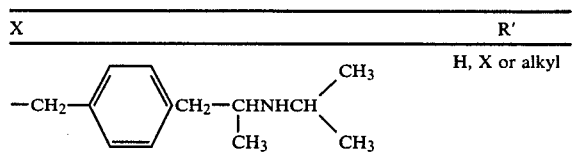 | H, X or alkyl |

-continued

| X | R' |
|---|---|
| —CH$_2$—⟨benzene⟩—CH$_2$—NCH$_2$(CH$_2$)$_e$N(CH$_3$)$_2$ with CH$_3$ branch, where e is 1 or 2 | H, X or alkyl |
| —(CH$_2$)$_f$NH—CH(CH$_3$)$_2$ where f is 2 or higher | H, X or alkyl |
| —(CH$_2$)$_g$N(CH$_3$)$_2$ where g is 2 or higher | H, X or alkyl |
| —(CH$_2$)$_h$N⟨piperidine⟩ where h is 2 or higher | H, X or alkyl |
| —(CH$_2$)$_i$—N⟨morpholine⟩O where i is 2 or higher | H, X or alkyl |

Typical technetium-99m complexes according to the invention have structures as follows:

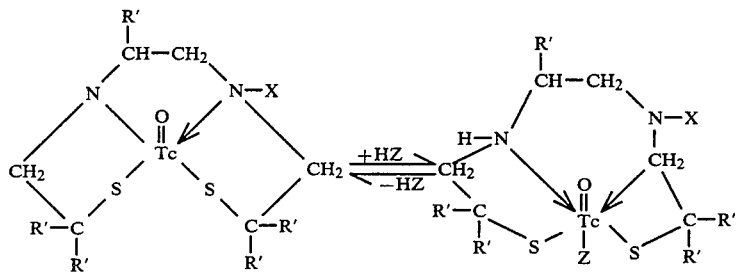

The compounds of the invention wherein the alkyl-amino side chain is attached to a nitrogen atom are synthesized from disulfides such as the following:

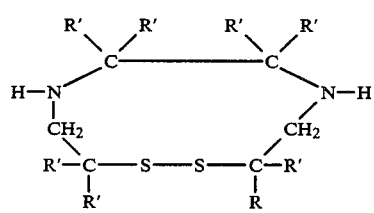

Compound 1

Synthesis of these starting materials is already known, see Corbin, Journal of Organic Chemistry, Vol. 41, pages 489–491(1976). The following is illustrative of the sequence of reaction steps which are used, commencing with those starting materials:

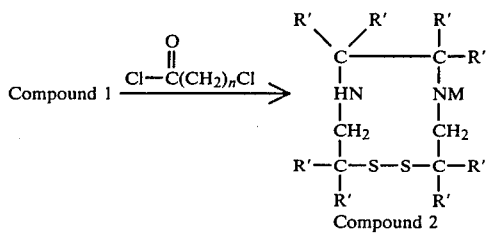

where M is

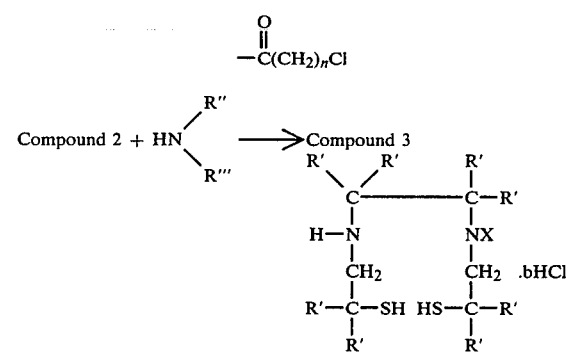

The imaging compounds are formed easily by reaction of a reducing agent such as stannous chloride or sodium dithionite with the ligand and sodium or ammonium pertechnate (Tc-99m). Nearly quantitative yields are obtained.

Biodistribution studies have been conducted with several complexes according to the present invention, in ICR white mice. A saline solution containing 0.5 to 2 microcuries of the Tc-99m complex was injected intravenously (tail), and the mice were sacrificed after 5, 10 or 15 minutes. The percent of the injected dose which was present in brain tissue was measured. The results of these studies are given in Table 1. The data show that compounds containing the alkyl-amino side chain are taken up in the brain only a little more slowly than the corresponding compound wherein the alkyl-amino side chain is replaced with a hydrogen atom. On the other hand, the data reveal that the compounds containing the alkyl-amino group according to the present invention are retained in the brain for much longer times. For example, after 15 minutes, the concentration of compound 3 is 15 times that of compound 1.

In table 1, the compounds have the general formula:

TABLE 1

$$\begin{array}{c} CR'_2\text{————}CH_2 \\ | \qquad\qquad\qquad | \\ H\text{—}N \qquad\qquad N\text{—}X \\ | \qquad\qquad\qquad | \\ CH_2 \qquad\qquad CH_2 \\ | \qquad\qquad\qquad | \\ CH_3\text{—}C\text{—}SH \quad HS\text{—}C\text{—}CH_3 \\ | \qquad\qquad\qquad | \\ CH_3 \qquad\qquad CH_3 \end{array}$$

| | | | % of Dose of $Tc_{99m}$ Complex in Brain | | |
|---|---|---|---|---|---|
| Compound | R' | X | 5 min | 10 min | 15 min |
| 1 | H | —H | 1.02 | 0.30 | 0.03 |
| 2 | H | —(CH$_2$)$_2$N(CH$_3$)$_2$ | 0.89 | 0.30 | 0.42 |
| 3 | H | —(CH$_2$)$_2$NHCH(CH$_3$)$_2$ | 0.64 | 0.49 | 0.49 |
| 4 | H | (N—morpholino)ethyl $+$CH$_2\rightarrow_2$N—(CH$_2\rightarrow_2$O$+$CH$_2\rightarrow_2$ | | | |
| 5 | H | (N—piperidinyl)ethyl $+$CH$_2\rightarrow_2$N$+$CH$_2\rightarrow_5$ | | | |
| 6 | CH$_3$ | —(CH$_2$)$_2$N(CH$_3$)$_2$ | | | |
| 7 | CH$_3$ | —(CH$_2$)$_2$NHCH(CH$_3$)$_2$ | | | |
| 8 | CH$_3$ | (N—morpholino)ethyl $+$CH$_2\rightarrow_2$N—(CH$_2\rightarrow_2$O$+$CH$_2\rightarrow_2$ | | | |
| 9 | CH$_3$ | (N—piperidinyl)ethyl $+$CH$_2\rightarrow_2$N$+$CH$_2\rightarrow_5$ | 2.19 | — | 1.01 |

The compounds of the invention are primarily useful in humans, although they may have veterinary applications. They may be injected intravenously at a dose of 10 to 20 millicuries per 70 kg person (with appropriate adjustment according to weight) and imaging is conducted by known procedures. The compounds may typically be formulated in saline solution containing 0.9% salt and 10 to 20 millicuries of the compound in 0.1 to 1 ml.

The following is a general procedure for the synthesis of the imaging agents of the present invention.

1. Preparation of Chloroacetamide Derivative (Compound 2) from Diaminodisulfide (Compound 1).

1 gram (4.27 mmole) of the diaminodisulfide (Compound 1) and 30 ml toluene are added to a flask, and the solution is stirred. 2.89 gram (25.1 mmole) of chloroacetylchloride is added dropwise. As the acid chloride is added, a milky suspension is formed. After the addition is complete, the flask is capped and the contents are allowed to stir for several hours or preferably overnight. The mixture is then filtered, and the filtrate is neutralized with dilute, aqueous sodium hydroxide. It is then extracted with three successive 50 ml portions of diethyl ether. The ether extracts are combined, washed with 10 ml water, dried over sodium sulfate, filtered and evaporated to remove ether under reduced pressure. The unevaporated residue is a white solid. It is purified by recrystallization from methaol.

2. Conversion of the Chloroacetamide Derivative (Compound 2) to the Aminoamide Derivative (Compound 3).

A flask equipped with a reflux condenser and a stirrer is loaded with the product of the preceding step, 5–7 equivalents of amine and 20–40 ml of absolute methanol or ethanol. The resulting solution is refluxed overnight. The volatiles are then removed by evaporation under reduced pressure, and the residue is basified with dilute aqueous sodium hydroxide. The aqueous phase is extracted with ether and the extracts are treated and evaporated as in the previous step. The crude product is recrystallized from pentane to afford crystals if the initial product is solid.

3. Preparation of triaminodithiol trihydrochloride.

In a flask, 1.92 mmole of the aminoacetamide derivative (Compound 3) is dissolved in 40 ml tetrahydrofuran which has been freshly dried over sodium and benzophenone and distilled. 280 mg (7.38 mmole) lithium aluminum hydride is added in small portions. The flask is equipped with a stirrer and condenser, and the contents of the flask are refluxed for 8 hours. The reaction may be monitored by infrared spectroscopy for the disappearance of the amide carbonyl groups, but 2 hours is generally a sufficient time for the reaction to occur. The mixture is cooled and the reaction is quenched by the addition of a saturated solution of ammonium chloride. The volatile solvent is evaporated, leaving a white residue which is triturated in ethanol. The triturant is filtered and evaporated, leaving a white residue; the residue is dissolved in 4 ml water, and the pH is adjusted to 9, providing a cloudy solution. That solution is extracted with two successive 10 ml portions of diethyl ether, and the ether layers are combined, dried over sodium sulfate, filtered and evaporated to provide a pale yellow to purple viscous residue, which is the free base dithiol. The dithiol is redissolved in ether and passed through a small silica gel column (0.5–2 cm). To the emerging colorless effluent, hydrochloric acid is added, and a white precipitate is formed. The ether is evaporated, leaving the trihydrochloride salt.

4. Labeling with Tc-99m

2–4 mg of the ligand is dissolved in 0.7 ml saline (0.9%) with 5–10 millicuries of sodium pertechnate (Tc-99m) and 0.1 ml of stannous chloride solution (prepared by dissolving 2–4 mg stannous chloride in 100 ml absolute alcohol). The mixture is reacted for ½ hour at room temperature. Then a few drops of aqueous sodium hydroxide (0.1N) are added to adjust the pH to 11. The product is transferred to a rubber capped test tube and extracted three times with successive 1 ml portions of hexane in a vortex mixer. The hexane extracts are evaporated to dryness under nitrogen. The product is then redissolved in 0.5 ml ethanol, and diluted to a specific activity of 50 microcuries per 5 ml in saline.

For the preparation of the technetium 99 complex, 1.2 millimoles of the ligand is stirred with 1 millimole of ammonium pertechnate (99m) in 40 ml of a solution containing ethanol and water in a 1:3 ratio. A solution containing 1.3 millimoles of sodium dithionate in 8 ml of 2N sodium hydroxide is added slowly, and the mixture is stirred at room temperature for 3 hours. The volume is reduced by evaporation until crystals form, and the crystals are separated by filtration. The crystals are washed with water, air dried and recrystallized from a mixture containing acetonitrile and water in a 2:1 ratio. If the product fails to crystallize, it may be extracted into methylene chloride; the organic layer is washed twice with water and dried over sodium sulfate. The product then can be crystallized by adding 80 ml petroleum ether. It is then recrystallized as described above.

It will be understood that the invention has been described by reference to preferred embodiments. It will be appreciated that changes may be made in details of composition, synthetic methods and modes of administration without departing from the scope of the invention, as defined in the appended claims.

What is claimed is:

1. A compound of the structure:

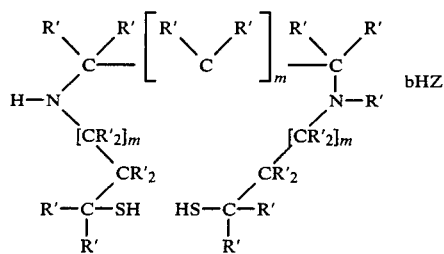 bHZ wherein each R' is independently a hydrogen atom, an alkyl group or X, and at least one of the groups R' is X, m is 0 or 1, Z is the anion of a strong mineral acid, b is an integer of 2 or greater and X has the formula:

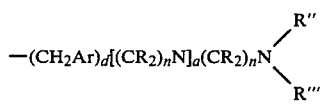

where R is hydrogen or an alkyl group, R'' and R''' are independently hydrogen atoms or alkyl groups, Ar is an aromatic group, and a, d and n are 0 or integers.

2. A compound as set forth in claim 1 in which Ar is phenylene.

3. A compound as set forth in claim 1 in which a and d are 0 or 1 and n is 2 or 3.

4. A compound as set forth in claim 1 in which b is 2 or 3.

5. A compound as set forth in claim 3 in which Z is chloride.

6. A compound of the formula:

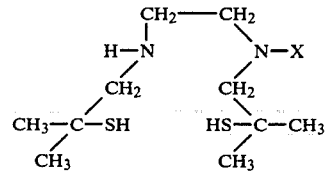

wherein X is $-(CH_2)_2N(CH_3)_2$.

7. A compound of the formula:

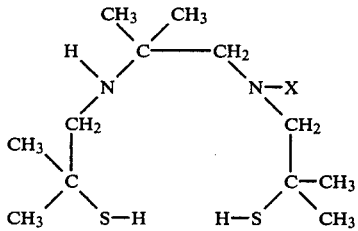

wherein X is $-(CH_2)_2NHCH(CH_3)_2$.

8. A compound of the formula:

wherein X is $-(CH_2)_2N-CH_2)_5$.

9. A coordination compound comprising the technetium 1:1 complex of the compound set forth in claim 1.

* * * * *